US010885680B2

(12) United States Patent
Noguchi

(10) Patent No.: US 10,885,680 B2
(45) Date of Patent: Jan. 5, 2021

(54) MEDICAL IMAGING DEVICE, IMAGE PROCESSING METHOD, AND PROGRAM

(71) Applicant: Hitachi, Ltd., Tokyo (JP)

(72) Inventor: Yoshimi Noguchi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 79 days.

(21) Appl. No.: 16/342,267

(22) PCT Filed: Jan. 23, 2018

(86) PCT No.: PCT/JP2018/001959
§ 371 (c)(1),
(2) Date: Apr. 16, 2019

(87) PCT Pub. No.: WO2018/155046
PCT Pub. Date: Aug. 30, 2018

(65) Prior Publication Data
US 2019/0236819 A1  Aug. 1, 2019

(30) Foreign Application Priority Data

Feb. 21, 2017 (JP) .................................. 2017-030236

(51) Int. Cl.
*G06T 11/00* (2006.01)
*A61B 5/00* (2006.01)
(Continued)

(52) U.S. Cl.
CPC ............ *G06T 11/008* (2013.01); *A61B 5/055* (2013.01); *A61B 5/726* (2013.01); *A61B 6/032* (2013.01);
(Continued)

(58) Field of Classification Search
CPC ................. G06T 11/008; G06T 11/006; G06T 2211/432; G06T 2211/424; A61B 6/5205;
(Continued)

(56) References Cited

U.S. PATENT DOCUMENTS

| 2010/0128958 A1 | 5/2010 | Chen |
| 2017/0035364 A1 | 2/2017 | Noguchi |

FOREIGN PATENT DOCUMENTS

| JP | 2012-509722 A | 4/2012 |
| JP | 2015-205037 A | 11/2015 |
| WO | WO-2016/208503 A1 | 12/2016 |

OTHER PUBLICATIONS

International Preliminary Report on Patentability issued in corresponding International Application No. PCT/JP2018/001959 dated Sep. 6, 2019.
(Continued)

*Primary Examiner* — Christopher Wait
(74) *Attorney, Agent, or Firm* — Foley & Lardner LLP

(57) ABSTRACT

In a medical imaging device that performs compressed sensing, it is possible to shorten a reconstruction time while maintaining image quality.
The medical imaging device includes an image reconstructing unit that reconstructs an image by performing an iterative optimization operation of compressed sensing and a base selecting unit that selects a base transform which is used for the optimization every iteration. The base selecting unit may select a base on the basis of a predetermined base sequence or may select a base using weighting factors which are set for the bases in advance. The invention is applied to a medical imaging device such as an MRI apparatus, an ultrasonic imaging apparatus, or a CT apparatus.

13 Claims, 11 Drawing Sheets

(51) Int. Cl.
    *A61B 6/03*     (2006.01)
    *A61B 8/14*     (2006.01)
    *A61B 5/055*    (2006.01)
    *A61B 6/00*     (2006.01)
    *A61B 8/08*     (2006.01)
(52) U.S. Cl.
    CPC .............. *A61B 6/5205* (2013.01); *A61B 8/14* (2013.01); *A61B 8/5207* (2013.01); *G06T 11/006* (2013.01); *G06T 2211/424* (2013.01); *G06T 2211/432* (2013.01)
(58) Field of Classification Search
    CPC ....... A61B 8/5207; A61B 5/726; A61B 6/032; A61B 8/14; A61B 5/055
    See application file for complete search history.

(56) References Cited

OTHER PUBLICATIONS

Lustig et al., "Sparse MRI: The Application of Compressed Sensing for Rapid MR Imaging" Magnetic Resonance in Medicine, 58:1182-1195, 2007.
Guo, Lei et al., "Wavelet-Based Compressive Sensing for Head Imaging", ISAP2015 International Symposium [online], Apr. 7, 2016 [Search: Apr. 6, 2018], internet: URL:http://ieeexplore.ieee.org/document/74477325.
International Search Report with English translation and Written Opinion issued in corresponding application No. PCT/JP2018/001959 dated Apr. 24, 2018.

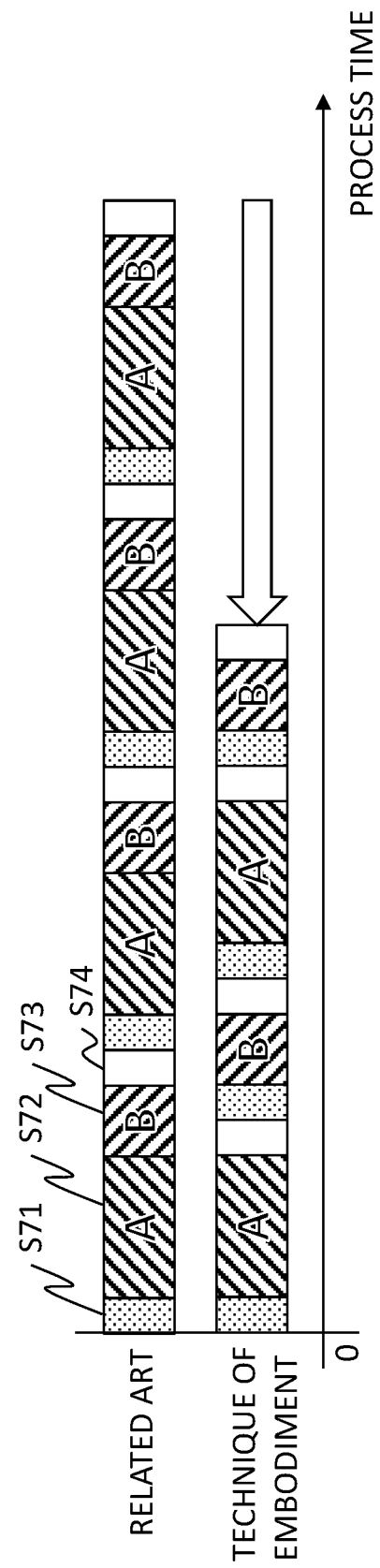

MEDICAL IMAGING DEVICE, IMAGE PROCESSING METHOD, AND PROGRAM

TECHNICAL FIELD

The present invention relates to image processing in a medical imaging device and particularly to a technique of increasing a processing speed thereof.

BACKGROUND ART

An imaging apparatus such as a magnetic resonance imaging (MRI) apparatus, a computed tomography (CT) apparatus, or an ultrasonic imaging apparatus is widely used as a medical imaging device. Among these apparatuses, an MRI apparatus is a medical diagnostic apparatus that can acquire tomographic images in a living body using a nuclear magnetic resonance (NMR) phenomenon and has merits that physical information which cannot be acquired using a CT apparatus, which is similarly capable of acquiring tomographic images, can be acquired, there is no radiation exposure, and the like. On the other hand, an MRI apparatus generally requires several tens of minutes for one examinee and thus has a low examination throughput, and an increase in processing speed thereof is required from the viewpoint of patient burden and hospital management.

Regarding this problem, high-speed imaging techniques using compressed sensing (CS) in addition to parallel imaging which have been hitherto used have been studied (Non-Patent Document 1 and Patent Document 1). Compressed sensing is a technique capable of reconstructing an original signal (image) from small observation results with high accuracy using sparseness of signals. An increase in imaging speed can be achieved by reducing the number of observation points, but there is a problem in that a calculation cost required for reconstruction is high and a time is required until an image is provided to a user, because iterative optimization is used.

CITATION LIST

Non-Patent Document

Non-Patent Document 1: Lustig et al., "Sparse MRI: The Application of Compressed Sensing for Rapid MR Imaging" Magnetic Resonance in Medicine, 58 1182-1195, 2007

Patent Document

Patent Document 1: JP-A-2015-205037

SUMMARY OF THE INVENTION

Technical Problem

In an iterative optimization operation of compressed sensing, a data restoring process including a base transform (also referred to as a sparse transform) or a cost minimizing process is performed on observed sparse data and the optimization operation is repeated using the restored data as an initial value. Various base transforms such as a wavelet transform and a curvelet transform are known as the base transforms which are used in the iterative operations, and image quality is expected to be improved using a plurality of base transforms. In the related art, predetermined base transforms or combinations thereof are determined in advance and the iterative optimization operation is performed using a combination of base transforms which is determined every iteration.

In order to increase a processing speed of the iterative optimization operation having a high calculation cost, it is conceivable that the number of iterations be reduced or a parameter (a threshold value) defining the iteration be changed, but reduction in the number of iterations or change of the threshold value for an increase in speed causes a decrease in image quality.

An objective of the invention is to shorten a reconstruction time while maintaining image quality and thus to improve a throughput of a medical imaging device such as an MRI apparatus.

Solution to Problem

In order to achieve the above-mentioned objective, the invention provides a configuration including a reconstruction unit configured to reconstruct an image using compressed sensing and a base selecting unit configured to select a base transform which is used for iterative optimization in the reconstruction unit.

Specifically, according to the invention, there is provided a medical imaging device including: an imaging unit configured to collect data which is required for image reconstruction from an examination object; and a data processing unit configured to process data which is collected by the imaging unit, in which the data processing unit includes an image reconstructing unit configured to perform an iterative operation on sparse data collected by the imaging unit by using a plurality of base transforms to reconstruct an image and a base selecting unit configured to select abase transform whose number is smaller than the plurality of base transforms which are used for the iterative operation, the base transform which is selected by the base selecting unit differs in at least two iterations, and the image reconstructing unit performs the iterative operation using the base transform which is selected by the base selecting unit.

According to the invention, there is provided an image processing method of reconstructing an image by performing an iterative optimization operation using a plurality of base transforms on sparse observed data which is acquired by an imaging unit of a medical imaging device, the image processing method including: selecting one base transform or a smaller number of base transforms than the plurality of base transforms from the plurality of base transforms; and performing an iterative operation using the base transform which differs in at least two iterations.

Advantageous Effects of the Invention

According to the invention, it is possible to shorten an imaging time and a reconstruction time in a medical imaging device and to acquire an image with high quality.

BRIEF DESCRIPTION OF THE DRAWINGS

FIG. 7 is a diagram illustrating an effect of processing in the first embodiment.

FIG. 8 is a functional block diagram of an image reconstructing unit according to a second embodiment.

FIG. 14 is a functional block diagram of an image reconstructing unit according to the fourth embodiment.

MODE FOR CARRYING OUT THE INVENTION

Hereinafter, an embodiment of a medical imaging device according to the invention will be described.

Figure 1:
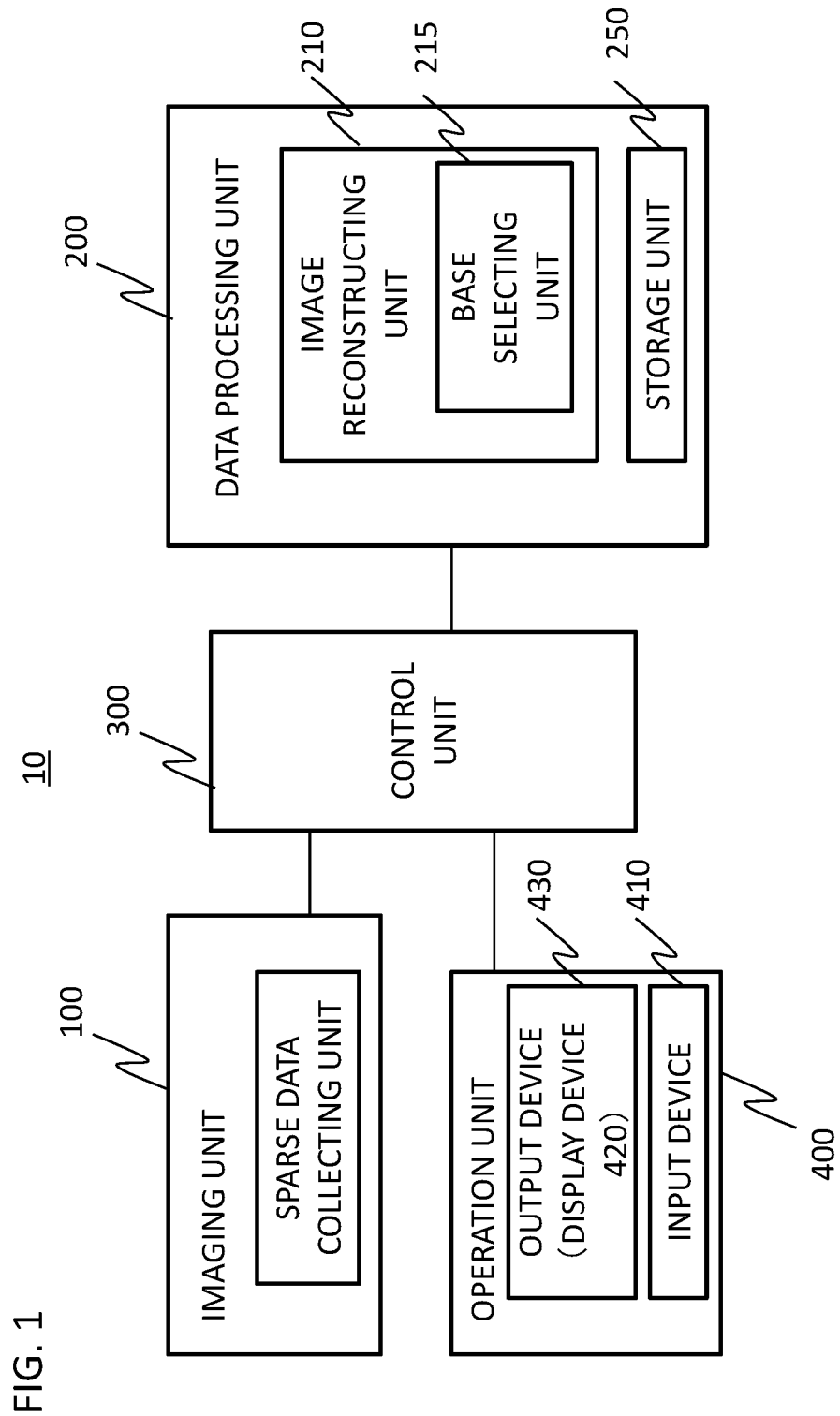
FIG. 1 is a diagram illustrating an outline of a medical imaging device.

The outline of the medical imaging device according to an embodiment is illustrated in FIG. 1. As illustrated in the drawing, a medical imaging device 10 roughly includes an imaging unit 100, a data processing unit 200, a control unit 300, and an operation unit 400.

The imaging unit 100 is a unit that collects information (observed data) which is acquired from an examinee and includes a static magnetic field generating magnet, a gradient magnetic field coil, a transmission and reception radio-frequency (RF) coil, and drive devices thereof in case of an MRI device. In case of a CT apparatus, the imaging unit 100 includes an X-ray source, an X-ray detector, a rotating plate, and drive devices thereof. Although detailed configurations of the units will be described later, all the imaging units collect observed data which can be converted into an image representing such as a shape of an examinee.

The data processing unit 200 includes an image reconstructing unit 210 that performs restoration of data using a compressed sensing technique and an operation of reconstructing an image of an examinee using sparse observed data which is collected by the imaging unit 100 and a storage unit 250 that stores data and the like during processing or data required for processing. The data processing unit 200 may be connected to an external storage device which is not illustrated and can store an operation algorithm which is used in an iterative operation which is performed by the image reconstructing unit 210 and a selection criterion or a selection rule thereof in the external storage device or in the storage unit 250.

The operation unit 400 includes an input device 410 such as a mouse and a keyboard which is used for a user to input conditions or commands to the data processing unit 200 or the control unit 300 and an output device 430 that outputs process results of the data processing unit 200 or an image. The output device 430 includes a printer or a display device 420. The display device also serves as an input device that displays a GUI for user input.

The control unit 300 controls operations of the imaging unit 100 and the data processing unit 200. The data processing unit 200 and the control unit 300 include the same or separate central processing units (CPU), and operations which are performed by the data processing unit 200 and control which is performed by the control unit 300 are embodied by causing the CPU to execute an incorporated program. A part of the function of the data processing unit 200 or the control unit 300 may be embodied in hardware such as an ASIC or an FPGA.

Figure 2:
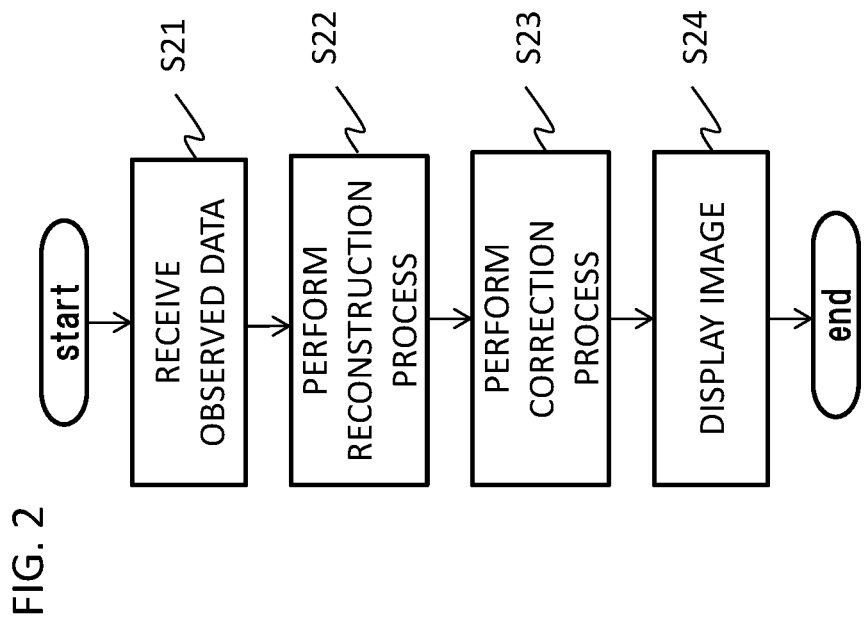
FIG. 2 is a diagram schematically illustrating an operation of the medical imaging device.

In the medical imaging device 10, as illustrated in FIG. 2, when the data processing unit 200 receives sparse observed data collected by the imaging unit 100 (S21), the image reconstructing unit 210 first performs an iterative operation based on compressed sensing to reconstruct an image (S22). This operation may be performed on the observed data itself or may be performed on image data into which the observed data has been converted. A process such as correction is performed if necessary (S23) and then a reconstructed image is generated. The reconstructed image generated by the image reconstructing unit 210 is displayed on the output device (for example, the display device) 430 as a display image if necessary (S24).

Figure 3:
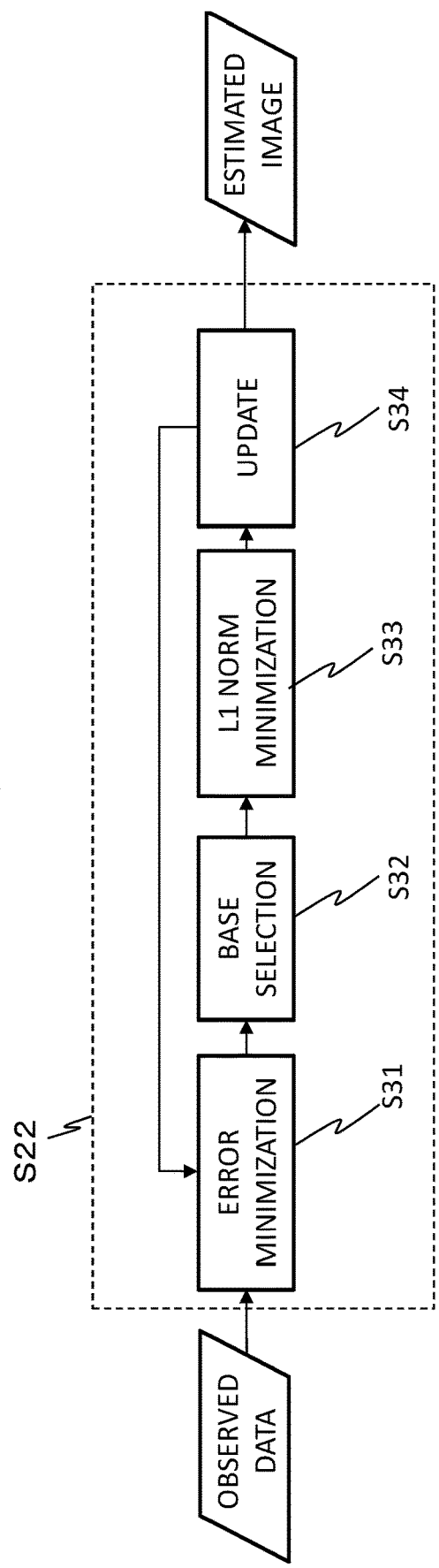
FIG. 3 is a diagram illustrating a processing example of an iterative operation in the medical imaging device according to an embodiment.

The iterative operation S22 which is performed by the image reconstructing unit 210 includes, for example, an error minimizing process S31, an L1 norm minimizing process (sparse transform process) S33, an update process S34, and the like as illustrated in FIG. 3, and observed data with a minimized error is acquired by repeating these processes. The L1 norm minimizing process is a process using a predetermined base transform. Examples of the base transforms include a wavelet transform, a curvelet transform, a Total Variation (TV), a discrete cosine transform (DCT), a Fourier transform, a Karhunen-Loeve transform (KLT), and the like. The accuracy of the iterative operation is improved by using a combination of a plurality of base transforms. The image reconstructing unit 210 according to this embodiment includes abase selecting unit 215 and performs a process S32 of selecting a base transform every iteration. The base selecting unit 215 selects types of base transforms or a combination thereof which are used in the L1 norm minimizing process S33 every iteration on the basis of a predetermined selection criterion. Although the selection criterion will be described in detail in the following embodiments, it is possible to prevent extension of a calculation time due to use of a plurality of base transforms and to enable an iterative operation into which a plurality of base transforms are incorporated by performing the iterative operation while changing the base transforms used in the process S33 every iteration in this way.

In the conventional method, the base transforms which are used for the iterative operation are fixed to predetermined ones, and a calculation load for each iteration is greater when a plurality of types of base transforms are used. On the other hand, in this embodiment, a base transform whose number is smaller than a plurality of types of base transforms are selected therefrom, and processing is performed, and selection of the base transforms and processing using the selected base transforms are performed every iteration. Accordingly, it is possible to achieve enhancement in calculation accuracy using a plurality of base transforms and it is possible to reduce a calculation load (a process cost) because the number of base transforms for each iteration can be reduced. The accuracy of observed data which is reproduced every iteration can be enhanced and the optimal base transforms can also be changed. In this embodiment, since a base transform is selected every iteration, it is possible to efficiently perform an iterative operation.

Embodiments in which the invention is applied to a specific medical imaging device will be described below.

First Embodiment

Figure 4:
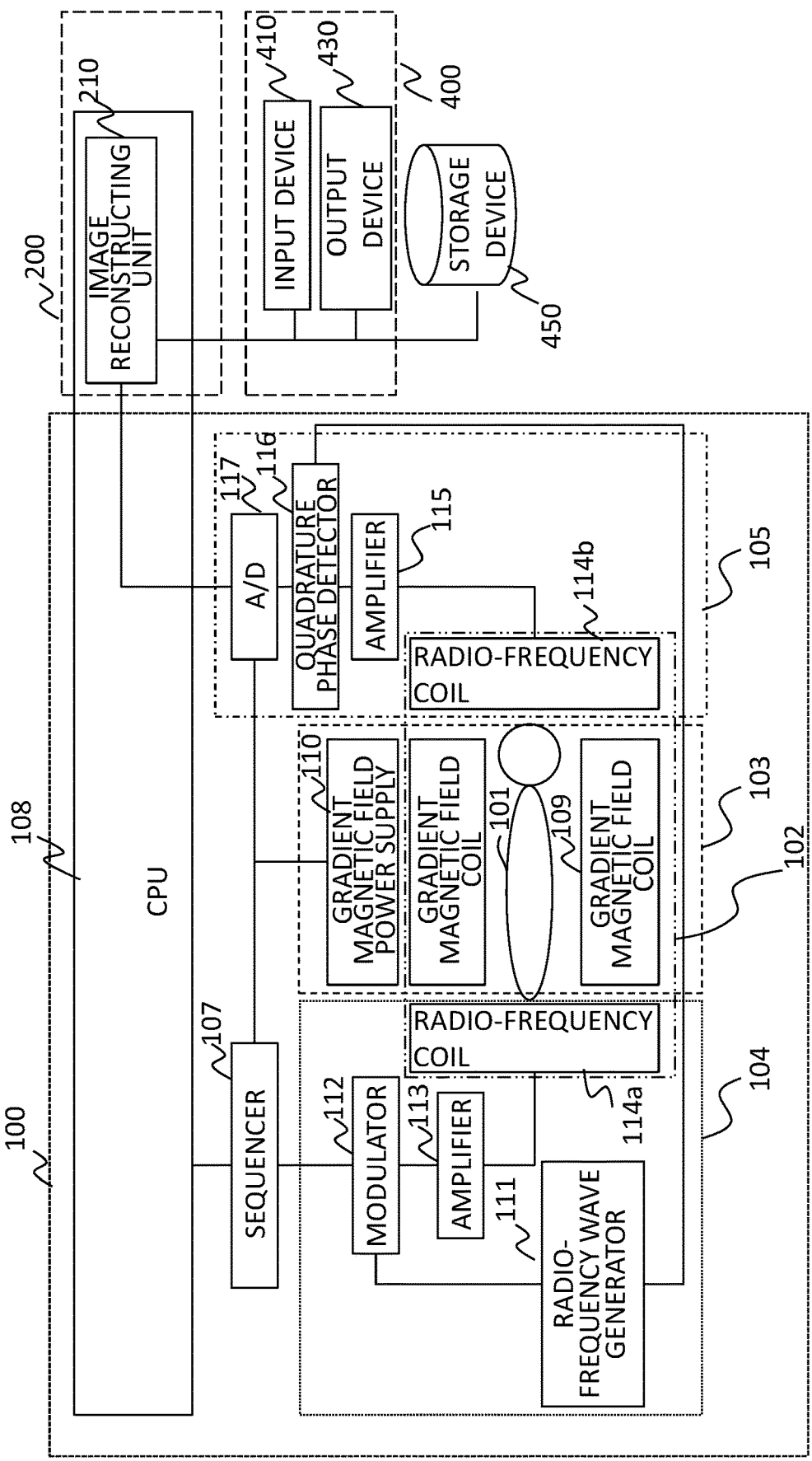
FIG. 4 is a diagram illustrating an example of the entire configuration of an MRI apparatus which is a medical imaging device according to a first embodiment.

In this embodiment, the processing of the data processing unit will be described using an MRI apparatus as an example. The configuration of the imaging unit 100 of the MRI apparatus is the same as a known MRI apparatus, and includes a static magnetic field generating unit 102, a gradient magnetic field generating unit 103, a transmitting unit 104, a receiving unit 105, a sequencer 107, and a central processing unit (CPU) 108 as principal elements as illustrated in FIG. 4. As the static magnetic field generating unit 102, a permanent magnet or a resistive or ultrasonic magnetic field generating means that generates a uniform magnetic field is disposed in a space around an examinee 101. The gradient magnetic field generating unit 103 includes a gradient magnetic field coil 109 and a gradient magnetic field power supply 110 that drives the gradient magnetic field coil 109, and applies a gradient magnetic field to the examinee 101.

The sequencer 107 is a control means that repeatedly applies a radio-frequency magnetic field pulse (an RF pulse) and a gradient magnetic field pulse in a predetermined pulse sequence, operates under the control of the CPU 108, and transmits various commands required for collecting data of tomographic images of the examinee 101 to the transmitting unit 104, the gradient magnetic field generating unit 103, and the receiving unit 105. The transmitting unit 104 includes a radio-frequency wave generator 111, a modulator 112, an amplifier 113, and a radio-frequency coil 114a, and applies an RF pulse for causing nuclear spins of atoms of the examinee 101 to generate nuclear magnetic resonance. The receiving unit 105 includes a radio-frequency coil 114b, an amplifier 115, a quadrature phase detector 116, and an A/D converter 117, receives echo signals which are emitted by nuclear magnetic resonance of nuclear spins, and transmits the received echo signals to the data processing unit 200.

The data processing unit 200 includes an image reconstructing unit 210 that mainly performs an operation for reconstructing an image. The data processing unit 200 also includes, as incidental devices, an input device 410 including such as a keyboard, a mouse, a touch panel, and buttons, includes an output device 430 including such as a display and a printer, and includes a storage device 450 including such as a magnetic disc and an optical disk and storing data or desired programs. Herein, it is assumed that a display device 420 is provided as the output device 430.

Figure 5:
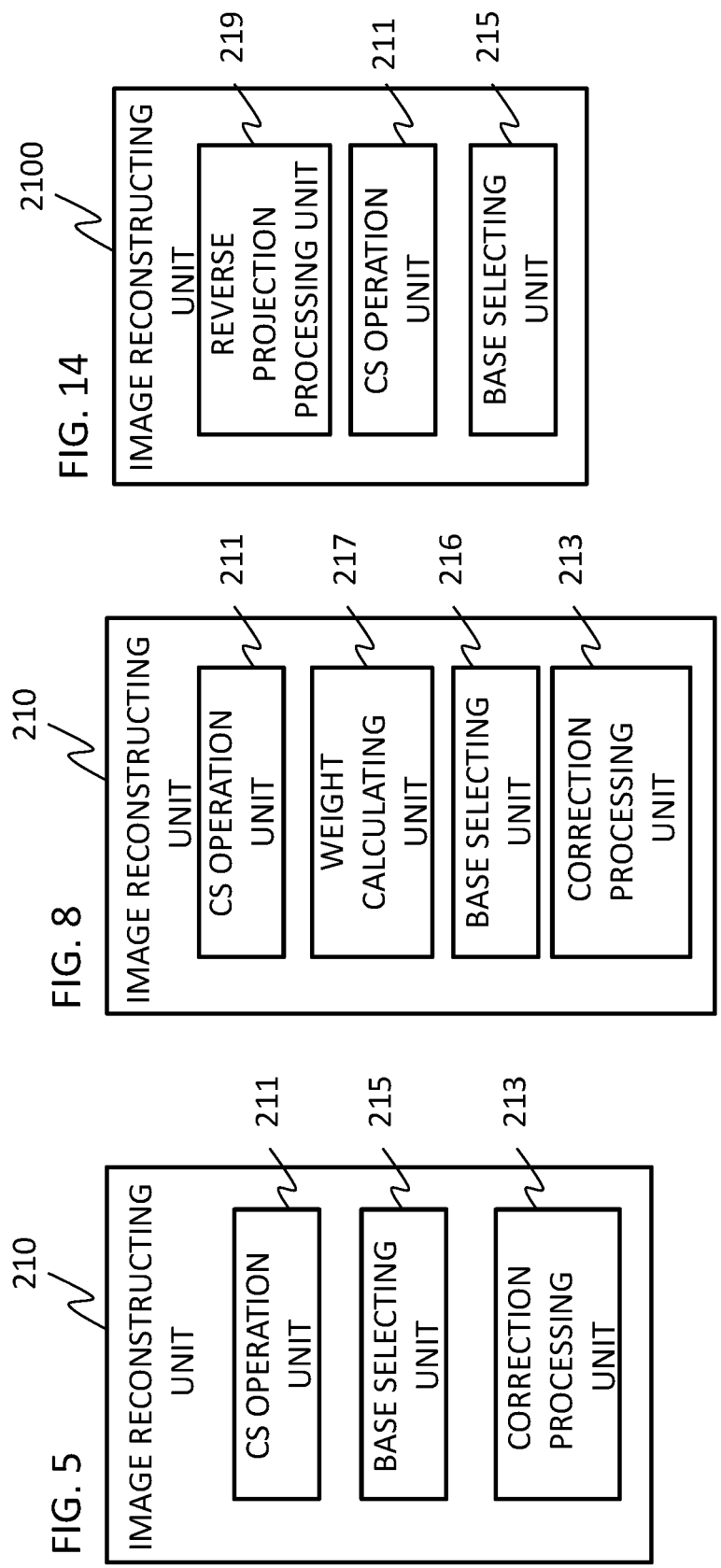
FIG. 5 is a functional block diagram of an image reconstructing unit according to the first embodiment.

When data is input from the receiving unit 105, the image reconstructing unit 210 reconstructs an image, causes the display device 420 to display the reconstructed image, and stores the reconstructed image in the storage device 450. As illustrated in FIG. 5, the image reconstructing unit 210 includes a CS operation unit 211 that performs a compressed sensing process on sparse observed data imaged (observed) by the imaging unit 100 and reconstructs an image, a correction processing unit 213 that performs a correction process such as noise removal or edge emphasis on the reconstructed image if necessary, and a base selecting unit 215 that selects a base transform which is used for the iterative operation of the compressed sensing every iteration.

The functions of the image reconstructing unit 210 can be embodied as program processes by the CPU 108 as illustrated in FIG. 4, and a central processing unit (CPU) other than the CPU 108 of the imaging unit 100 or a graphics processing unit (GPU) may be provided in the data processing unit 200, or some or all of the functions of the image reconstructing unit 210 may be configured in dedicated hardware for processing an image.

In consideration of the above-mentioned configuration, the processes of the image reconstructing unit 210 will be described below.

First, compressed sensing which is performed by the CS operation unit 211 will be described.

Compressed sensing is a technique of estimating a real signal X on the assumption that an observed signal Y is observed using the following expression through an observation process A.

[Math. 1]

$$Y = AX \tag{1}$$

In general, the estimated value X is acquired by solving a cost minimization problem expressed by the following expression.

[Math. 2]

$$\min\left(\frac{1}{2}(Y - AX)^2 + \tau|X|_1\right) \tag{2}$$

Here, $|\ |_1$ is referred to as an L1 norm. $\tau$ is a positive parameter for adjusting the balance between a square error (the first term in a large parenthesis of Expression (2)) and the L1 norm. Various methods are known as the cost minimization method and any method may be used. In this embodiment, a case in which a split Bregman method which is a kind of variable separation method is used will be described with reference to the flowcharts illustrated in FIG. 6.

[Initialization S61]

Sparse observed data which is collected by the imaging unit 100 is read and initial values of coefficients ($u_s$, $b_s$) and parameters are set. The observed data which is collected by the imaging unit 100 of the MRI apparatus is k-space data, and the sparse observed data is data obtained by thinning out data in a phase encoding direction in a k space, data obtained by thinning radial data in case of radial scan, or data obtained by collecting dots in the k space.

[Error Minimization S62]

The image reconstructing unit 210 (the CS operation unit 211) minimizes a square error from an observed signal. Specifically, an estimated image u is calculated using the following expressions. Herein, it is assumed that the number of iterations is i=k+1.

[Math. 3]

$$u^{k+1} = \frac{1}{2\mu+1}\Phi^T f^k + \frac{1}{2}\left(I_N - \frac{1}{2\mu+1}\Phi^T\Phi\right)(u_S^k - b_S^k) \tag{3}$$

Here, $f^k$ represents a frequency component of an image which is calculated in the previous (k-th) iteration, $\Phi$ represents an observation process including an image transform process (Fourier transform), and $\Phi^T$ represents an inverse transform process of $\Phi$. $I_N$ is a matrix of which all the elements are 1 and which has the same size as $f^k$. $u_s^k$ and $b_s^k$ are change components which are calculated in the previous (k-th) iteration. $\mu$ is a positive constant as a parameter.

[Base Selection S63]

The base selecting unit 215 selects one base transform which is used in the corresponding iteration process. Candidates of the base transform include known orthogonal transforms such as a TV, a wavelet transform, a curvelet transform, a ridgelet transform, a contourlet transform, a Fourier transform, a discrete cosine transform, and a KLT transform.

In this embodiment, it is assumed that the base transforms as the candidates are sequentially used and a current iteration count is used as a selection criterion. For example, when the iteration count is i (i-th iteration), the base transform which is selected out of N base candidates ($\Psi_0, \ldots, \Psi_{N-1}$) is $\Psi_d$ using the remainder d when the iteration count i is dividing by N. The sequence of the base transforms is not particularly limited, and may be determined in advance in consideration of characteristics (predicted characteristics) of observed data and the like.

[L1 Norm Minimization S64]

An L1 norm is minimized using the base transform which is selected by the base selecting unit 215. A shrinkage process is generally known as a method of minimizing an L1 norm. A soft-shrinkage process which is a kind of shrinkage process is defined by the following expression.

[Math. 4]

$$S(u^{k+1}+b_S^k) = \begin{cases} \Psi(u^{k+1}+b_S^k) - \frac{|\lambda|}{\mu} & \text{if } \Psi(u^{k+1}+b_S^k) \geq \frac{|\lambda|}{\mu} \\ \Psi(u^{k+1}+b_S^k) + \frac{|\lambda|}{\mu} & \text{if } \Psi(u^{k+1}+b_S^k) \leq -\frac{|\lambda|}{\mu} \\ 0 & \text{if } |\Psi(u^{k+1}+b_S^k)| < \frac{|\lambda|}{\mu} \end{cases} \quad (4)$$

Here, S denotes a shrinkage process and $\lambda$ is a parameter.

Inverse transform is performed by Expression (5) on the right side of Expression (4) and a (k+1)-th, that is, i-th, change component $u_s^{k+1}$ is calculated.

[Math. 5]

$$u_S^{k+1} = \Psi^T S(u^{k+1}+b_S^k) \quad (5)$$

In addition, $b_s^k$ is calculated by Expression (6).

[Math. 6]

$$b_S^{k+1} = b_S^k + u^{k+1} - u_S^{k+1} \quad (6)$$

[Update S65]

An update vector is calculated from the coefficients which are calculated through the L1 norm minimization S64. The parameters are updated if necessary.

Until the iteration count i reaches a predetermined count m, the above-mentioned processes S61 to S64 are repeated. That is, in the (k+1)-th process, the processes subsequent to the error minimization step S62 is performed using the update vector calculated in S64 as an initial value.

[End Determination S66]

In the example illustrated in the drawing, the iterative operation ends at a time point at which the iteration count reaches a predetermined count m, but the determination of ending the iteration may be performed using the magnitude of the update vector and a difference from the previous estimation result as ending conditions in addition to the iteration count. That is, the time point at which the update vector or the difference becomes equal to or less than a predetermined magnitude (a threshold value) is used as an ending condition.

Through the above-mentioned processes, an estimated image is obtained. The estimated image is real-space data which is obtained by performing the Fourier transform on the k-space data. The estimated image is subjected to a correction process such as noise removal or edge emphasis by the correction processing unit 213 and is processed into a display image, and the display image is displayed on the display device 420 and is also stored in the storage device 450.

As described above, according to this embodiment, it is possible to shorten the reconstruction time while maintaining the image quality of a reconstructed image due to combining a plurality of base transforms. In FIG. 7, a result of comparison in reconstruction time between the related art and this embodiment when four iterative operations are performed using two base transforms is illustrated as a simplified example. Reference signs S71 and S74 in the drawing correspond to the processes S61 and S65 in FIG. 6 which has been described above, and reference signs S72 and S73 correspond to the L1 norm minimization S64 using base transforms A and B which are different types.

In the related art, the process S64 (S72+S73) is performed using a plurality of base transforms every iteration. On the other hand, in this embodiment, the base transform is changed every iteration and a plurality of base transforms are used as the whole processes. Accordingly, the reconstruction time in this embodiment is greatly shortened in comparison with that in the related art, and the finally obtained restored image can be maintained in the same image quality as in the related art because a plurality of base transforms are used for L1 norm minimization.

Second Embodiment

In the first embodiment, the base selecting unit 215 selects a base transform on the basis of a predetermined base transform sequence. On the other hand, in this embodiment, it is possible to more rapidly acquire a reconstructed image with high image quality by dynamically changing the selection criterion for selecting a base.

In this embodiment, the entire configuration of the device is the same as in the first embodiment and description thereof will not be repeated. The process of the image reconstructing unit, particularly, the base selecting unit 215, in this embodiment will be described below with a focus on a difference from the first embodiment.

Figure 6:
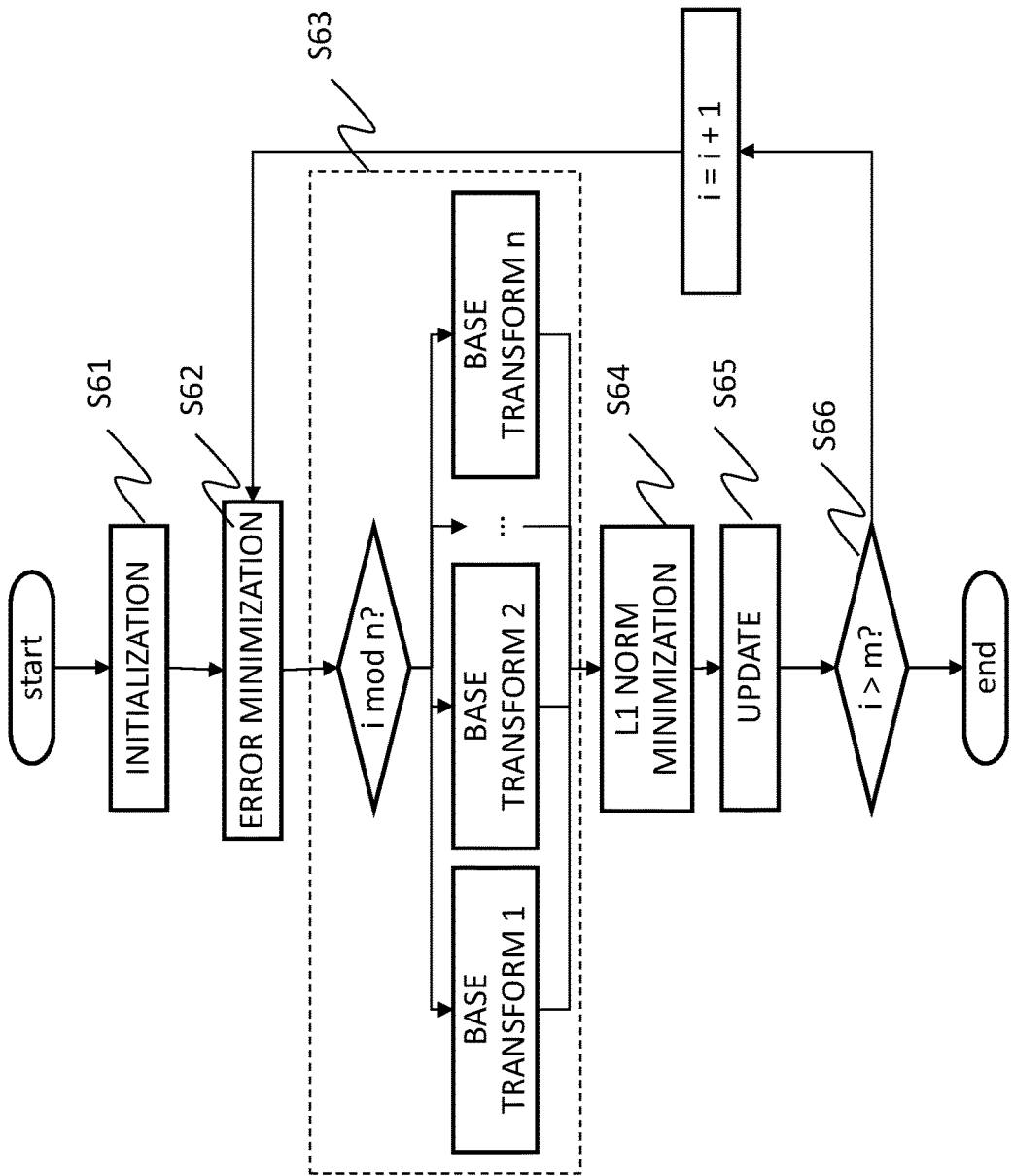
FIG. 6 is a diagram illustrating a process flow which is performed by the image reconstructing unit according to the first embodiment.

An example of the image reconstructing unit according to this embodiment is illustrated in FIG. 8. In FIG. 8, the same elements as the elements illustrated in FIG. 5 will be referred to by the same reference signs and description thereof will not be repeated. In this embodiment, a weight calculating unit 217 is added to the image reconstructing unit 210. The weight calculating unit 217 calculates weights for controlling selection of a base in the base selecting unit 216. Accordingly, the process details of the base selecting unit 216 are different from those of the base selecting unit 215 in the first embodiment. The process flow in the image reconstructing unit is the same as that in the first embodiment except that details of the base selecting process S63 in FIG. 6 are changed, and FIG. 6 will be referred to for if necessary.

The processes of the weight calculating unit 217 and the base selecting unit 216 will be described below.

The weight calculating unit 217 calculates a weight w for each base transform and transmits the calculated weight to the base selecting unit 216. The weight w is a vector of the same dimension as the number of base transform candidates and generally has a value of 0 to 1.

One out of the L1 norm after each base transform has been performed, the magnitude of the update vector, a user's taste transmitted from the input unit, and an imaging parameters transmitted from the imaging unit 100 or the like, or a combination thereof is used for calculating the weight.

When the L1 norm after the base transform has been performed is used, the weight calculating unit 217 first transforms observed data using the base transforms as candidates and calculates the magnitude of the L1 norm. Then, the weight calculating unit 217 calculates a weighting factor to be in inverse proportion to the magnitude of the L1 norm. Accordingly, a base transform which can be performed more sparsely is likely to be selected. Regarding the magnitude of the update vector, the magnitude of the update vector after transform has been performed is calculated using each base transform as the candidates and the weighting factor is calculated to be in inverse proportion thereto.

Figure 9A:
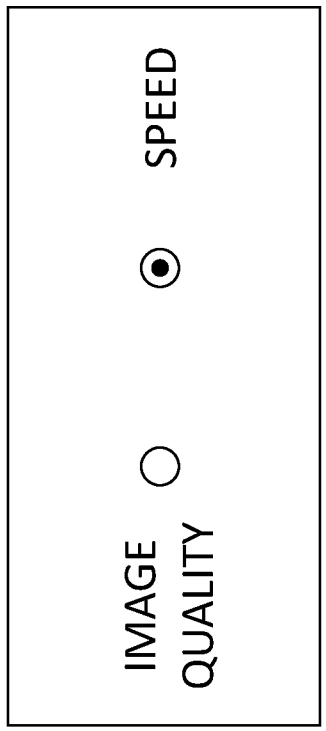
FIGS. 9(A) to 9(C) are diagrams illustrating examples of a screen of an input unit according to the second embodiment.
Figure 9B:
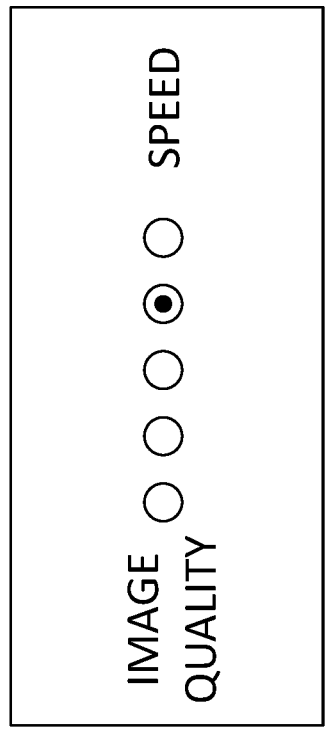
Figure 9C:
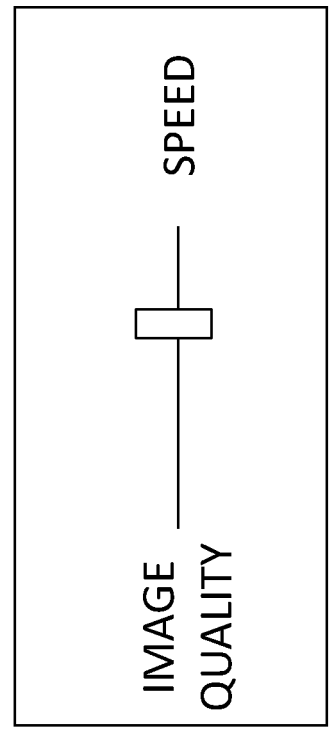

When a user's taste is introduced, a user input screen (GUI) is displayed on the display device 420. Examples of an input screen which is presented to a user are illustrated in FIGS. 9(A) to 9(C). In the examples illustrated in the drawings, for example, which of image quality and a processing speed has priority (a presented example: FIG. 9(A)) or a balance therebetween (presented examples: FIGS. 9(B) and 9(C)) is input. The input device 410 transmits data input from a user to the weight calculating unit 217. The weight calculating unit 217 stores data obtained by measuring a process time required for each base transform in advance. When a user gives a priority to the processing speed, it is possible to improve the processing speed by setting the weight of a base transform which can be performed in a higher speed to be greater. Regarding the image quality, a relationship between the number of iterations of the operation (the process time) and an SN ratio for each base transform may be stored in advance as data and the weight for each base transform may be set on the basis of the relationship.

When imaging parameters are used, first, the imaging unit 100 transmits the imaging parameters which are used at the time of observation, such as an imaged region, a sequence, a slice thickness, a field of view (FOV), and a matrix size, to the weight calculating unit 217. Since an observed image varies greatly depending on the imaging conditions in the MRI, the weight calculating unit 217 defines a weight table for each region and sequence in advance. For example, in a time of flight (TOF) image, a blood vessel has a very strong signal value and high contrast. In this case, since the TV or the wavelet transform has a high speed and high efficiency, the weights of these base transforms are set to be great. Accordingly, it is possible to acquire a reconstructed image with high image quality at a high speed.

The weight calculating unit 217 transmits the calculated weighting factors of the base transforms to the base selecting unit 216. The weighting factors may be stored in the storage unit 250 or the storage device 450.

The base selecting unit 216 determines a base selection sequence using the weights w which are transmitted from the weight calculating unit 217. Here, abase transform candidate of which the weight is 0 or is equal to or less than a predetermined threshold value may be excluded from the selection candidates. Various methods are considered as the method of determining a selection sequence using the weights, and any method can be used. For example, a method using the weight as a selection probability of each base transform is known as the simplest method. This method is, for example, a method of randomly selecting one base transform from base transform candidates including five As, three Bs, and two Cs on the assumption that A, B, and C are three types of base transform candidates and the weight w is calculated as w=(0.5, 0.3, 0.2). This method has a likelihood that a specific base transform will be biased when the number of iterations is small.

Figure 10:
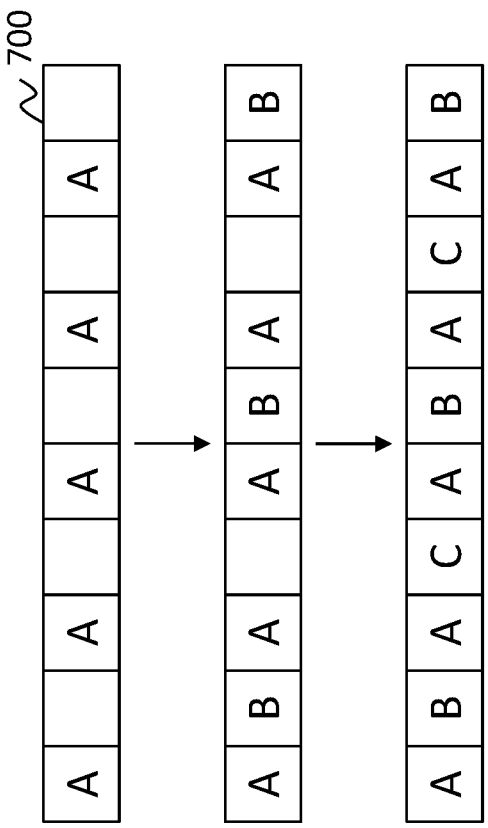
FIG. 10 is a diagram illustrating a process of calculating a selection sequence in a base selecting unit according to the second embodiment.

As another method, a method of generating a sequence with frequencies corresponding to the weight can be used. This method will be described below when the weight w is calculated as w=(0.5, 0.3, 0.2) with respect to the above-mentioned three types of base transform candidates A, B, and C. The procedure of calculating a sequence table is illustrated in FIG. 10.

First, the weight is arranged in the form of a ratio and is defined as the number of selections. In this example, the weight ratio is 5:3:2. At this time, the weight may be made as integers using an appropriate threshold value. Then, a selection sequence table 700 corresponding to the total number of selections is generated. In this example, the total number of selections is 10. The selection sequence table is filled in the descending order of the number of selections such that selection intervals are equal. For example, since the number of selection of base A is 5, the base transform is filled as illustrated in the upper part of FIG. 10. By sequentially filling bases B and C as illustrated in the middle and lower parts of FIG. 10, an unbiased selection sequence can be generated. For each iteration, the base selecting unit 216 selects a base on the basis of the calculated sequence table 700. When the number of iterations is greater than the magnitude of the sequence table 700, the selection sequence is returned to the head of the sequence table 700.

Two methods are described above as the method of determining the selection sequence, and these methods may be combined. For example, the second method may be employed in a stage in which the number of iterations is small, and then may be switched to the method using the weight as a selection probability of the base transforms.

After the sequence of base transforms has been determined by the base selecting unit 216, the L1 norm minimization S64 and the update S65 are repeated using the selected base transform in the same way as in the process flow of the image reconstructing unit according to the first embodiment until the number of iterations reaches a predetermined number.

According to this embodiment, a base transform can be selected from selectable base transforms in consideration of image quality or a process time. It is possible to acquire a reconstructed image with high image quality at a high speed. According to this embodiment, it is possible to perform image reconstruction in consideration of a user's taste.

Modified Examples

In the first embodiment and the second embodiment, one base transform is selected from a plurality of base transform candidates for each iteration of the CS operation, but the base selecting unit may select a plurality of base transforms from a plurality of base transform candidates. The number of base transforms to be selected for each iteration may vary.

When a plurality of bases are selected, various selection methods can be considered and any method may be employed. For example, a plurality of base transforms may be selected on the basis of a predetermined base transform sequence as in the first embodiment or may be selected using the weight as in the second embodiment.

Figure 11:
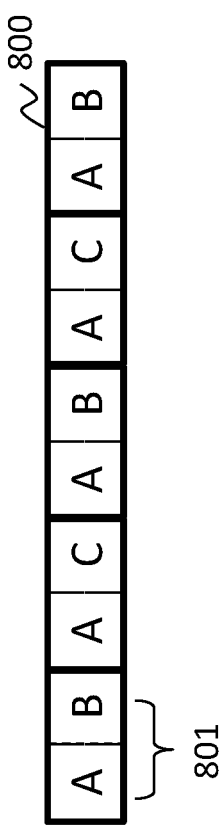
FIG. 11 is a diagram illustrating a process of calculating a selection sequence in the base selecting unit according to the second embodiment.

For example, the selection method using the weight when two types of bases are selected from three types of candidate bases will be described below. For example, similarly to the case in which one base is selected, two types of bases may be selected using the weight as a probability. Alternatively, as illustrated in FIG. 11, a sequence table 800 same as the sequence table 700 which is used to select one base in the second embodiment is prepared, and the sequence table 800 in which two frames (which are indicated by a bold line) 801 corresponding to two iterations as a group corresponds to one iteration is prepared. In the example illustrated in FIG. 11, the same base is not included in one frame, but there is a likelihood that the same base may be repeatedly included in one frame when the base transforms are selected using the weight or three or more types of base transforms are selected. In order to avoid this situation, a constraint condition that the same base is not to be selected may be set.

According to this modified example, when a signal for giving priority to image quality is transmitted from the input device 410 by a user's input or when the number of observation points of observed data is small, improvement in image quality can be expected by selecting a plurality of bases.

While embodiments in which the invention is applied to an MRI apparatus have been described above, the invention is not limited to an MRI apparatus and can be applied to any medical imaging device as long as it is a medical imaging device including an imaging unit that can acquire observed data having sparseness (sparse observed data) and a functional unit that reconstructs a medical image on the basis of the sparse observed data. In the following embodiments, examples of the medical image device other than an MRI apparatus will be described.

Third Embodiment

A third embodiment is an embodiment in which the medical imaging device is an ultrasonic diagnostic apparatus.

Figure 12:
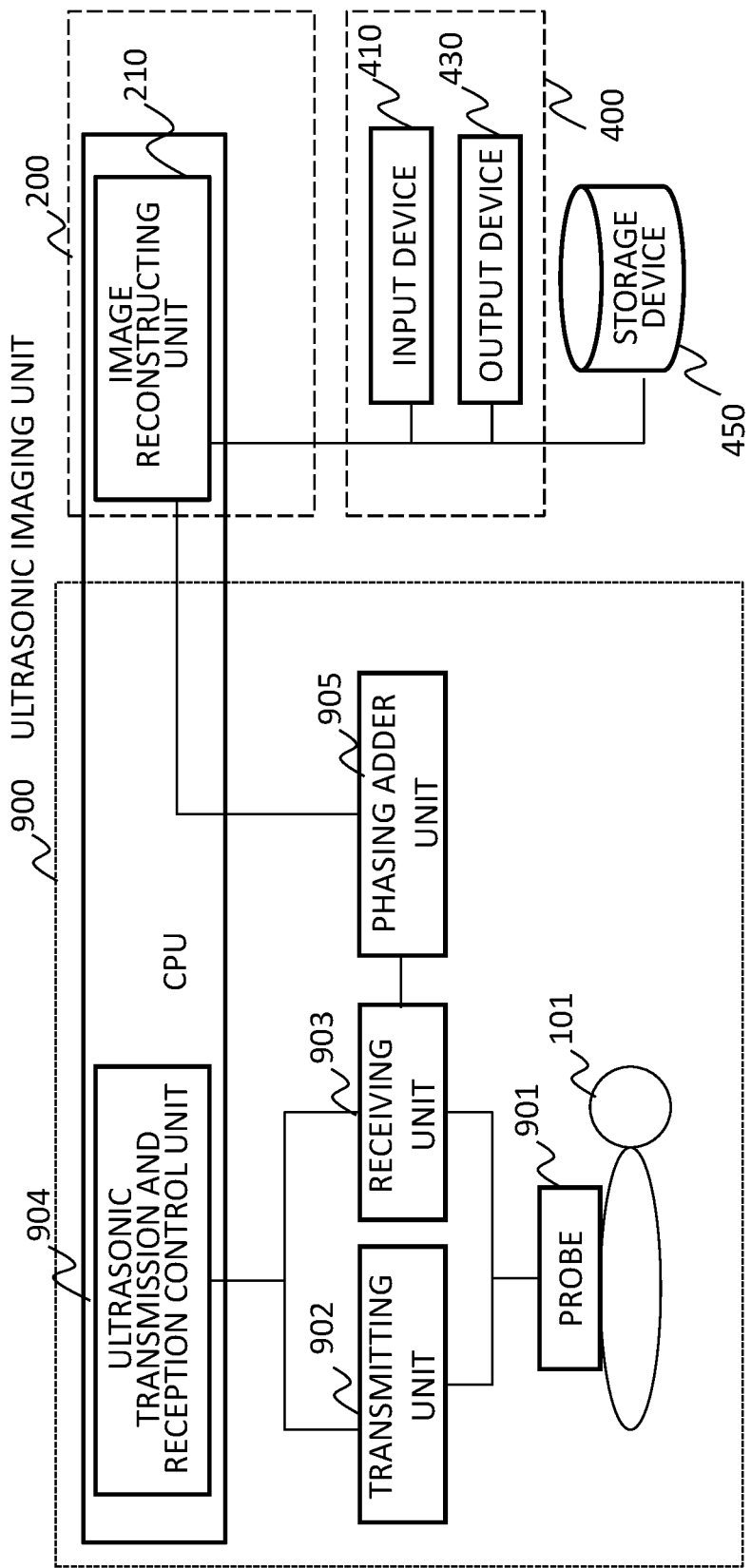
FIG. 12 is a diagram illustrating an example of an entire configuration of an ultrasonic diagnostic apparatus according to a third embodiment.

FIG. 12 illustrates an example of a configuration of an ultrasonic diagnostic apparatus as a medical imaging device according to the third embodiment. In FIG. 12, elements having the same functions as the elements illustrated in FIG. 4 will be referred to by the same reference signs and description thereof will not be repeated. As illustrated in the drawing, the ultrasonic diagnostic apparatus includes an ultrasonic imaging unit 900 including an ultrasonic probe 901, a transmitting unit 902, a receiving unit 903, an ultrasonic transmission and reception control unit 904, and a phasing adder unit 905.

The transmitting unit 902 iteratively transmits ultrasonic waves to an examinee 101 via the ultrasonic probe 901 at time intervals. The receiving unit 903 receives reflected echo signals in a time series which are generated from the examinee 101. The ultrasonic transmission and reception control unit 904 controls the transmitting unit 902 and the receiving unit 903. The phasing adder unit 905 phases and adds the received reflected echo signals and generates RF signal frame data in a time series. The phasing adder unit 905 has an analog-to-digital (A/D) converter built therein and outputs the RF signal frame data as observed data to the image reconstructing unit 210 of the data processing unit 200. The image reconstructing unit 210 generates an ultrasonic echo image using the RF signal frame data.

At this time, the image reconstructing unit 210 performs a CS operation using the ultrasonic echo image as sparse observed data similarly to the first or second embodiment or the modified examples thereof. At this time, the base transform which is used for the CS operation is selected every iteration of the operation, processing using a plurality of base transforms is performed, and an ultrasonic image with high image quality is calculated at a high speed.

As described above, with the ultrasonic diagnostic apparatus according to this embodiment, it is possible to acquire an ultrasonic image with high image quality at a high speed.

Fourth Embodiment

A fourth embodiment is an embodiment in which the medical imaging device is a computed tomography (CT) apparatus that can acquire a CT image with high image quality.

Figure 13:
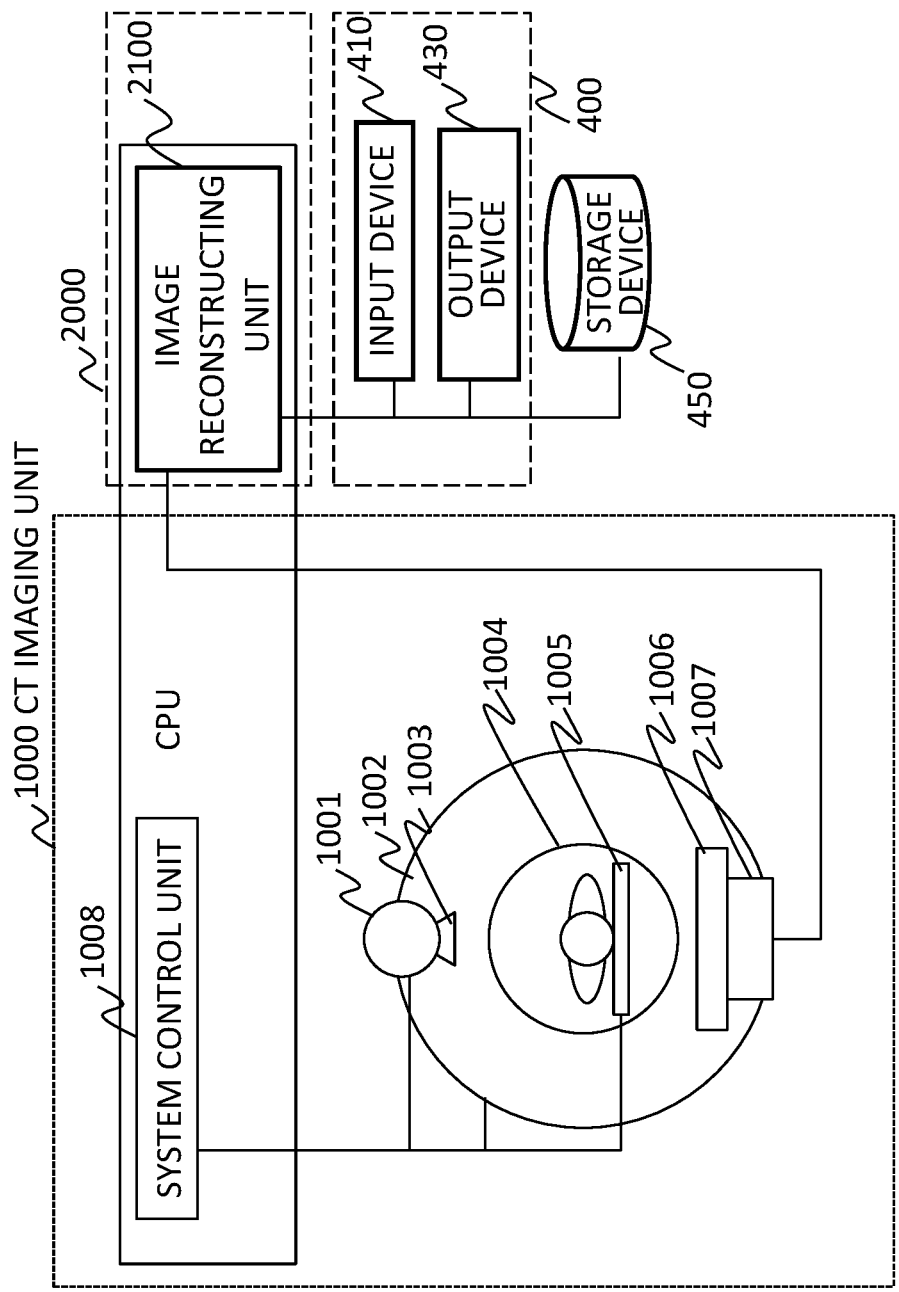
FIG. 13 is a diagram illustrating an example of an entire configuration of a CT apparatus according to a fourth embodiment.

FIG. 13 illustrates an example of a configuration of a CT apparatus as a medical imaging device according to this embodiment. In the drawing, elements having the same functions as the elements illustrated in FIG. 4 will be referred to by the same reference signs and description thereof will not be repeated.

In FIG. 13, a CT imaging unit 1000 includes an X-ray tube device 1001, a rotating disk 1002, a collimator 1003, an X-ray detector 1006, a data collecting device 1007, a bed 1005, and a system control unit 1008. The X-ray tube device 1001 is a device that irradiates an examinee placed on the bed 1005 with X-rays. The collimator 1003 is a device that limits a radiation range of X-rays which are emitted from the X-ray tube device 1001. The rotating disk 1002 includes an opening 1004 into which the examinee 101 placed on the bed 1005 is inserted, and has the X-ray tube device 1001 and the X-ray detector 1006 mounted thereon, and rotates around the examinee.

The X-ray detector 1006 is a device that is disposed to face the X-ray tube device 1001 and measures a spatial distribution of transmitted X-rays by detecting X-rays transmitted by the examinee, in which a plurality of X-ray detection elements are arranged in a rotating direction of the rotating disk 1002 or are arranged in two dimensions of the rotating direction and a rotation axis direction of the rotating disk 1002. The data collecting device 1007 collects an X-ray dose detected by the X-ray detector 1006 as digital data. The system control unit 1008 controls rotation of the rotating disk 1002, movement in all directions of the bed 1005, power input to the X-ray tube device 1001, and the like.

The CT imaging unit 1000 transmits observed data (projection data at each rotation angle) to an image reconstructing unit 2100 of a data processing unit 2000. As illustrated in FIG. 14, the image reconstructing unit 2100 includes a reverse projection processing unit 219 that generates a CT image using the projection data, a CS operation unit 211 that performs a CS operation on the CT image which is generated by the reverse projection processing unit 219, and a base selecting unit 215. Although not illustrated in FIG. 14, the image reconstructing unit 2100 may include a weight calculating unit or a correction processing unit similarly to FIG. 8, and the base selecting unit 215 is substituted with the base selecting unit 216 illustrated in FIG. 8 when it includes the weight calculating unit. A CT image which is generated by the reverse projection processing unit 219 is an image having X-ray absorption coefficients as pixel values and is sparse observed data on the assumption that the X-ray absorption coefficient is constant in the same tissue and varies in only the boundary of the tissue. Accordingly, the CT image is to be subjected to the CS operation using Expressions (3) and (4) which have been described above in the first embodiment. Similarly to the first or second embodiment or the modified examples thereof, the CS operation unit 211 performs processing using a plurality of base transforms while selecting abase transform for the CS operation every iteration of the operation using the sparse observed data and calculates a CT image with high image quality at a high speed.

As described above, according to the invention, it is possible to rapidly acquire a CT image with high image quality.

While embodiments of the invention have been described above, the invention is not limited to the above-mentioned embodiments and includes various modified examples. For example, the embodiments have been described in detail for the purpose of more understanding of the invention and the invention is not limited to the configurations including all the elements described therein. Some of the elements of a certain embodiment can be substituted with elements in another embodiment, and an element in a certain embodiment may be added to elements in another embodiment. Some of the elements in the embodiments may be subjected to addition, deletion, and substitution of another element.

An example in which a program, which is executed by a CPU, for embodying some or all of the above-mentioned elements, functions, processing units, and the like is prepared has been described above, but some or all thereof may be embodied in hardware, for example, by design as an integrated circuit.

REFERENCE SIGNS LIST

- 100 Imaging unit
- 101 Examinee
- 102 Static magnetic field generating unit
- 103 Gradient magnetic field generating unit
- 104 Transmitting unit
- 105 Receiving unit
- 108 Central processing unit (CPU)
- 109 Gradient magnetic field coil
- 110 Gradient magnetic field power supply
- 111 Radio-frequency wave generator
- 112 Modulator
- 113 Amplifier
- 114a, 114b Radio-frequency coil
- 200 Data processing unit
- 210 Image reconstructing unit
- 211 CS operation unit
- 213 Correction processing unit
- 215, 216 Base selecting unit
- 217 Weight calculating unit
- 250 Storage unit
- 300 Control unit
- 400 Operation unit
- 410 Input device
- 420 Display device
- 430 Output device
- 450 Storage device
- 900 Ultrasonic imaging unit
- 1000 CT imaging unit

The invention claimed is:

1. A medical imaging device comprising:
an imaging unit configured to collect data which is required for image reconstruction from an examination object; and
a data processing unit configured to process data which is collected by the imaging unit,
wherein the data processing unit includes an image reconstructing unit configured to perform an iterative operation on sparse data collected by the imaging unit by using a plurality of base transforms to reconstruct an image and a base selecting unit configured to select a base transform whose number is smaller than the plurality of base transforms which are used for the iterative operation,
the base transform which is selected by the base selecting unit differs in at least two iterations, and
the image reconstructing unit performs the iterative operation using the base transform which is selected by the base selecting unit.

2. The medical imaging device according to claim 1, wherein the base selecting unit selects the base transform in accordance with a predetermined sequence of the plurality of base transforms.

3. The medical imaging device according to claim 1, wherein the base selecting unit selects the base transform on the basis of at least one of a processing time using the base transform and image quality of an image which is acquired after the base transform has been performed.

4. The medical imaging device according to claim 1, further comprising a weight calculating unit configured to calculate weights for the plurality of base transforms,
wherein the base selecting unit selects the base transform using the weights calculated by the weight calculating unit.

5. The medical imaging device according to claim 4, further comprising an input unit that is used for a user to input an index for selecting the base transform,
wherein the weight calculating unit calculates the weights on the basis of the index input from the input unit.

6. The medical imaging device according to claim 4, wherein the weight calculating unit calculates the weights on the basis of imaging conditions which are used for the imaging unit to acquire the data.

7. The medical imaging device according to claim 6, wherein the base selecting unit prepares a selection sequence table in which a sequence for selecting the base transform is defined using the weights calculated by the weight calculating unit and selects the base transform on the basis of the selection sequence table.

8. The medical imaging device according to claim 1, wherein the medical imaging device is one of a magnetic resonance imaging apparatus, an ultrasonic imaging apparatus, and a computed tomography (CT) apparatus.

9. An image processing method of reconstructing an image by performing an iterative optimization operation using a plurality of base transforms on sparse observed data which is acquired by an imaging unit of a medical imaging device, the image processing method comprising:
selecting one base transform or a smaller number of base transforms than the plurality of base transforms from the plurality of base transforms; and
performing an iterative operation using the base transform which differs in at least two iterations.

10. The image processing method according to claim 9, wherein the base transform to be selected is changed every iteration.

11. The image processing method according to claim 9, further comprising a step of calculating weights for the plurality of base transforms,
   wherein the base transform for each iteration is selected on the basis of the weights.

12. The image processing method according to claim 9, wherein the base transform which is selected every iteration is one base transform and a plurality of base transforms are used in the iterative operation as a whole.

13. A program causing a computer to perform following steps A to E which are:
   Step A of calculating estimated data with a minimized error using sparse observed data, which is collected by a medical imaging device, as an initial value;
   Step B of selecting a smaller number of base transforms than a plurality of base transform candidates form the candidates;
   Step C of performing an L1 norm minimization on the estimated data calculated in the error minimization step A using the selected base transforms;
   Step D of updating the initial value in the error minimizing step using a coefficient acquired by the L1 norm minimization; and
   Step E of repeating Steps A to D until ending conditions are satisfied.

* * * * *